(12) United States Patent
Govari et al.

(10) Patent No.: US 9,737,353 B2
(45) Date of Patent: Aug. 22, 2017

(54) SYSTEM FOR CONTROLLING TISSUE ABLATION USING TEMPERATURE SENSORS

(75) Inventors: Assaf Govari, Haifa (IL); Yaron Ephrath, Karkur (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 265 days.

(21) Appl. No.: 12/969,684

(22) Filed: Dec. 16, 2010

(65) Prior Publication Data

US 2012/0157890 A1 Jun. 21, 2012

(51) Int. Cl.
A61B 18/00 (2006.01)
A61B 18/18 (2006.01)
(Continued)

(52) U.S. Cl.
CPC .......... *A61B 18/1206* (2013.01); *A61B 18/20* (2013.01); *A61B 5/01* (2013.01); *A61B 5/055* (2013.01); *A61B 18/1233* (2013.01); *A61B 18/1492* (2013.01); *A61B 18/24* (2013.01); *A61B 2017/00243* (2013.01); *A61B 2018/00023* (2013.01); *A61B 2018/00351* (2013.01); *A61B 2018/00577* (2013.01); *A61B 2018/00648* (2013.01); *A61B 2018/00702* (2013.01); *A61B 2018/00779* (2013.01);
(Continued)

(58) Field of Classification Search
USPC ....................... 128/898; 606/2–52
See application file for complete search history.

(56) References Cited

U.S. PATENT DOCUMENTS 5,005,147 A * 4/1991 Krishen ............... G06K 9/6293
703/13
5,122,137 A * 6/1992 Lennox .......................... 606/40
(Continued)

FOREIGN PATENT DOCUMENTS

JP 09-094252 A 4/1997
JP 11-155869 A 6/1999
(Continued)

OTHER PUBLICATIONS

Tempany et al., Focused ultrasound ablation offer prostate cancer option, Diagnostic Imaging, Jan. 1, 2009, retrieved from www.diagnosticimaging.com.*

(Continued)

*Primary Examiner* — Lynsey Crandall
*Assistant Examiner* — Manolis Pahakis
(74) *Attorney, Agent, or Firm* — Lewis Roca Rothgerber Christie LLP

(57) ABSTRACT

Body tissue ablation is carried out by inserting a probe into a body of a living subject, urging the probe into contact with a tissue in the body, generating energy at a power output level, and transmitting the generated energy into the tissue via the probe. While transmitting the generated energy the ablation is further carried out by determining a measured temperature of the tissue and a measured power level of the transmitted energy, and controlling the power output level responsively to a function of the measured temperature and the measured power level. Related apparatus for carrying out the ablation is also described.

14 Claims, 4 Drawing Sheets

(51) Int. Cl.

| | | |
|---|---|---|
| *A61B 18/12* | (2006.01) | |
| *A61B 18/20* | (2006.01) | |
| A61B 5/01 | (2006.01) | |
| A61B 5/055 | (2006.01) | |
| A61B 18/14 | (2006.01) | |
| A61B 18/24 | (2006.01) | |
| A61B 17/00 | (2006.01) | |
| A61N 7/02 | (2006.01) | |
| A61B 90/00 | (2016.01) | |

(52) U.S. Cl.
CPC ........... A61B 2018/00791 (2013.01); A61B 2090/374 (2016.02); A61B 2090/378 (2016.02); A61N 7/022 (2013.01)

(56) References Cited

U.S. PATENT DOCUMENTS

| | | | | |
|---|---|---|---|---|
| 5,540,681 | A * | 7/1996 | Strul et al. .................. | 606/34 |
| 5,542,916 | A * | 8/1996 | Hirsch et al. ................ | 604/22 |
| 5,573,533 | A * | 11/1996 | Strul ............................ | 606/34 |
| 5,626,140 | A * | 5/1997 | Feldman ............... | G06K 9/6293 600/483 |
| 5,688,267 | A * | 11/1997 | Panescu ............. | A61B 18/1492 606/31 |
| 5,743,903 | A * | 4/1998 | Stern et al. .................. | 606/31 |
| 5,755,715 | A * | 5/1998 | Stern ........................ | A61B 18/00 606/31 |
| 5,906,614 | A * | 5/1999 | Stern ........................ | A61B 18/12 606/31 |
| 6,092,033 | A * | 7/2000 | Uhlmann ................. | G06F 17/18 701/469 |
| 6,139,546 | A * | 10/2000 | Koenig et al. ................ | 606/34 |
| 6,226,542 | B1 | 5/2001 | Reisfeld | |
| 6,231,569 | B1 * | 5/2001 | Bek et al. .................... | 606/34 |
| 6,293,943 | B1 * | 9/2001 | Panescu .............. | A61B 18/1206 606/27 |
| 6,301,496 | B1 | 10/2001 | Reisfeld | |
| 6,356,790 | B1 | 3/2002 | Maguire et al. | |
| 6,558,378 | B2 * | 5/2003 | Sherman et al. ............. | 606/34 |
| 6,575,969 | B1 * | 6/2003 | Rittman, III et al. ......... | 606/41 |
| 6,814,733 | B2 | 11/2004 | Schwartz et al. | |
| 6,829,568 | B2 * | 12/2004 | Julier ...................... | G06F 17/18 702/189 |
| 6,892,091 | B1 | 5/2005 | Ben-Haim et al. | |
| 6,997,924 | B2 | 2/2006 | Schwartz et al. | |
| 7,065,465 | B2 * | 6/2006 | Chen et al. .................. | 702/116 |
| 7,156,816 | B2 | 1/2007 | Schwartz et al. | |
| 7,293,400 | B2 * | 11/2007 | Taware et al. .............. | 60/39.27 |
| 7,520,877 | B2 * | 4/2009 | Lee et al. .................... | 606/42 |
| 7,536,218 | B2 | 5/2009 | Govari et al. | |
| 7,594,913 | B2 * | 9/2009 | Ormsby et al. .............. | 606/33 |
| 2003/0078736 | A1 * | 4/2003 | Weng ...................... | G06F 19/20 702/19 |
| 2003/0184468 | A1 * | 10/2003 | Chen .................... | G06K 9/3241 342/52 |
| 2006/0074496 | A1 * | 4/2006 | Taware et al. ................ | 700/11 |
| 2006/0217707 | A1 * | 9/2006 | Daniel et al. ................. | 606/50 |
| 2007/0005306 | A1 * | 1/2007 | Foessel ................ | G01S 13/723 702/189 |
| 2007/0060832 | A1 | 3/2007 | Levin | |
| 2007/0076917 | A1 * | 4/2007 | Chen et al. .................. | 382/103 |
| 2007/0198007 | A1 * | 8/2007 | Govari et al. ................ | 606/34 |
| 2007/0208333 | A1 * | 9/2007 | Uchida et al. ................ | 606/34 |
| 2008/0071263 | A1 * | 3/2008 | Blaha ........................... | 606/35 |
| 2008/0281322 | A1 * | 11/2008 | Sherman et al. .............. | 606/42 |
| 2008/0287944 | A1 * | 11/2008 | Pearson et al. ................ | 606/41 |
| 2008/0300588 | A1 | 12/2008 | Groth et al. | |
| 2008/0319436 | A1 * | 12/2008 | Daniel et al. ................. | 606/33 |
| 2010/0179534 | A1 * | 7/2010 | Podhajsky et al. ........... | 606/34 |
| 2010/0262135 | A1 * | 10/2010 | Berube ........................ | 606/33 |
| 2010/0298826 | A1 * | 11/2010 | Leo et al. .................... | 606/41 |
| 2011/0137147 | A1 * | 6/2011 | Skliar ..................... | A61N 7/02 600/411 |
| 2011/0152857 | A1 * | 6/2011 | Ingle .................. | A61B 18/1206 606/40 |

FOREIGN PATENT DOCUMENTS

| | | |
|---|---|---|
| WO | WO 96/00036 A1 | 1/1996 |
| WO | WO 97/30647 A1 | 8/1997 |
| WO | WO 99/17672 A1 | 4/1999 |

OTHER PUBLICATIONS

Durrant-Whyte H., Multi Sensor Data Fusion, The University of Sydney, Jan. 22, 2001.*
U.S. Appl. No. 12/941,165, filed Nov. 8, 2010—pending.
EP Search Report No. EP 11 19 3722 Dated Jul. 4, 2012.
Tempany, Clare, M. D. et al. "Focused ultrasound ablation offer prostate cancer option." Diagnostic Imaging 31.1. Jan. 1, 2009.
Japanese Notification of Reasons for Refusal dated Nov. 10, 2015 in corresponding Japanese Application No. 2011-274253.

* cited by examiner

SYSTEM FOR CONTROLLING TISSUE ABLATION USING TEMPERATURE SENSORS

BACKGROUND OF THE INVENTION

1. Field of the Invention

This invention relates to invasive medical devices. More particularly, this invention relates to ablation of tissue using such devices.

2. Description of the Related Art

Ablation of body tissue using electrical energy is known in the art. The ablation is typically performed by applying alternating currents, for example radiofrequency energy, to the electrodes, at a sufficient power to destroy target tissue. Typically, the electrodes are mounted on the distal tip of a catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue.

Self-regulating tissue ablators have been proposed to achieve the desired control. For example, PCT International Publication WO 9600036 discusses ablation of body tissue in which ablating energy is conveyed individually to multiple emitters in a sequence of power pulses. The temperature of each emitter is periodically sensed and compared to a desired temperature established for all emitters to generate a signal individually for each emitter based upon the comparison. The power pulse to each emitter is individually varied, based upon the signal for that emitter to maintain the temperatures of all emitters essentially at the desired temperature during tissue ablation.

U.S. Patent Application Publication No. 2008/0300588 proposes performing ablation automatically by monitoring system parameters. When the ablation is complete, as determined by a processor based on its reading of the system parameters, RF energy delivery is halted. The determination is made, preferably without the need for user interaction, based upon the system parameters and a set of rules for determining completion. Parameters that may be monitored include power output.

SUMMARY OF THE INVENTION

There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

The level of ablator power (P) and the tissue temperature (T) are key factors in achieving precise control of the delivery of radiofrequency energy by the catheter electrode. Such control is important in achieving consistent therapeutic results, while avoiding excessive injury to surrounding tissues.

In embodiments of the present invention, radiofrequency (RF) electrical current applied by an ablator is controlled by feedback based on the tissue temperature and delivered power. The temperature is typically measured by a sensor, such as a thermocouple, in the catheter tip, although other means of temperature measurement may also be used.

There is provided according to embodiments of the invention a method of body tissue ablation, which is carried out by inserting a probe into a body of a living subject, urging the probe into contact with a tissue in the body, generating energy at a power output level, and transmitting the generated energy into the tissue via the probe. While transmitting the generated energy the method is further carried out by determining a measured temperature of the tissue and a measured power level of the transmitted energy, and controlling the power output level responsively to a function of the measured temperature and the measured power level.

According to aspects of the method, the generated energy may be radiofrequency energy, ultrasound energy or laser-produced light energy.

According to still other aspects of the method, determining a measured temperature is performed using magnetic resonance imaging analysis or ultrasound imaging analysis.

According to an additional aspect of the method, the measured temperature is an electrode temperature.

According to one aspect of the method, the function includes a multiplicative product of a power factor and a temperature factor.

According to an aspect of the method, the power factor includes a difference between the measured power level and a target power level, and wherein the temperature factor includes a difference between the measured temperature and a target temperature.

An aspect of the method controlling the power output level includes iteratively comparing the measured temperature and the measured power level with a predetermined temperature target value and a power target value, respectively, and responsively to comparing varying the power output level to establish a new power output level so as to approach a predetermined target power value.

Yet another aspect of the method comparing and varying the power output level are iterated 10 times per second.

A further aspect of the method comparing and varying the power output level are iterated 5-50 times per second.

In still another aspect of the method varying the power output level is performed by varying an electrical current component of the generated energy.

In an additional aspect of the method varying the power output level is performed by limiting an increment or decrement thereof so as not to exceed a predetermined limiting condition, wherein the limiting condition is selected from the group consisting of a maximum current, a minimum electrode temperature, a maximum electrode temperature, a maximum temperature of the tissue, and a maximum power demand.

There is provided according to embodiments of the invention an ablation apparatus, including a catheter having a distal portion for insertion into a body cavity of a living subject and configured to bring the distal portion into contact with a tissue in the body cavity, a power generator for generating energy at a power output level, an ablation electrode disposed on the distal portion, which is adapted to accept the energy from the power generator via the catheter and to conduct the energy to the tissue for ablation thereof, a temperature sensor disposed on the distal portion for determining a temperature of the ablation electrode. The ablation apparatus further includes a processor operative for determining a measured temperature of the tissue and a measured power level of the energy conducted through the ablation electrode for controlling the power output level responsively to a function of the measured temperature and the measured power level.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
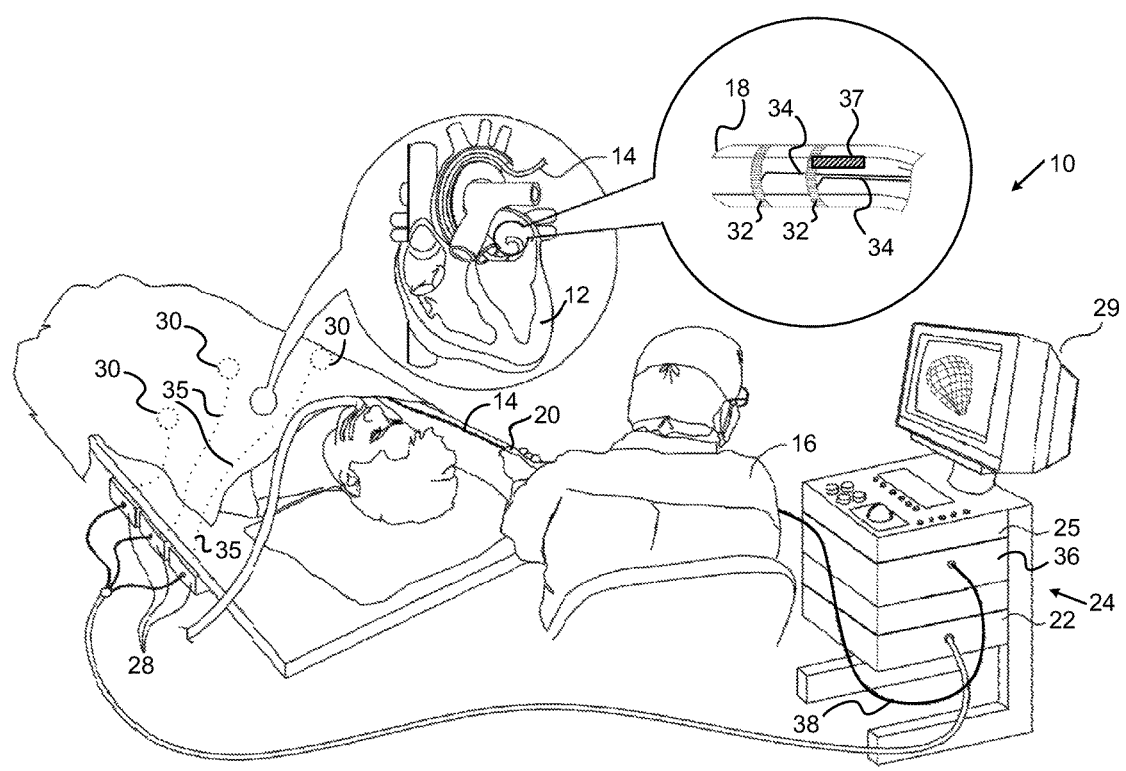
FIG. 1 is a pictorial illustration of a system for performing ablative procedures, which is constructed and operative in accordance with a disclosed embodiment of the invention.

Turning now to the drawings, reference is initially made to FIG. 1, which is a pictorial illustration of a system 10 for performing ablative procedures on a heart 12 of a living subject or patient, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. Although the embodiment described with respect to FIG. 1 is concerned primarily with cardiac ablation. The principles of the invention may be applied, mutatis mutandis, to body tissues other than the heart. One commercial product embodying elements of the system 10 is available as the CARTO 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers, to mapping in sinus rhythm, and when to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Electrical signals can be conveyed to and from the heart 12 through one or more electrodes 32 located at or near the distal tip 18 via wires 34 to the console 24. Pacing signals and other control signals may be conveyed from the console 24 through the wires 34 and the electrodes 32 to the heart 12. Additional wire connections 35 link the console 24 with body surface electrodes 30 and other components of a positioning sub-system. The electrodes 32 and the body surface electrodes 30 may be used to measure tissue impedance measuring at the ablation site as taught in U.S. Pat. No. 7,536,218, issued to Govari et al., which is herein incorporated by reference. A temperature sensor 37, typically a thermocouple or thermistor, is mounted on or near each of the electrodes 32.

The console 24 typically contains one or more ablation power generator 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning sub-system of the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume its vicinity and sensing these fields at the catheter using field generating coils 28.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of sensing electrodes (not shown) located distally in the catheter 14. The digitized signals are received and used by the console 24 and the positioning sub-system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
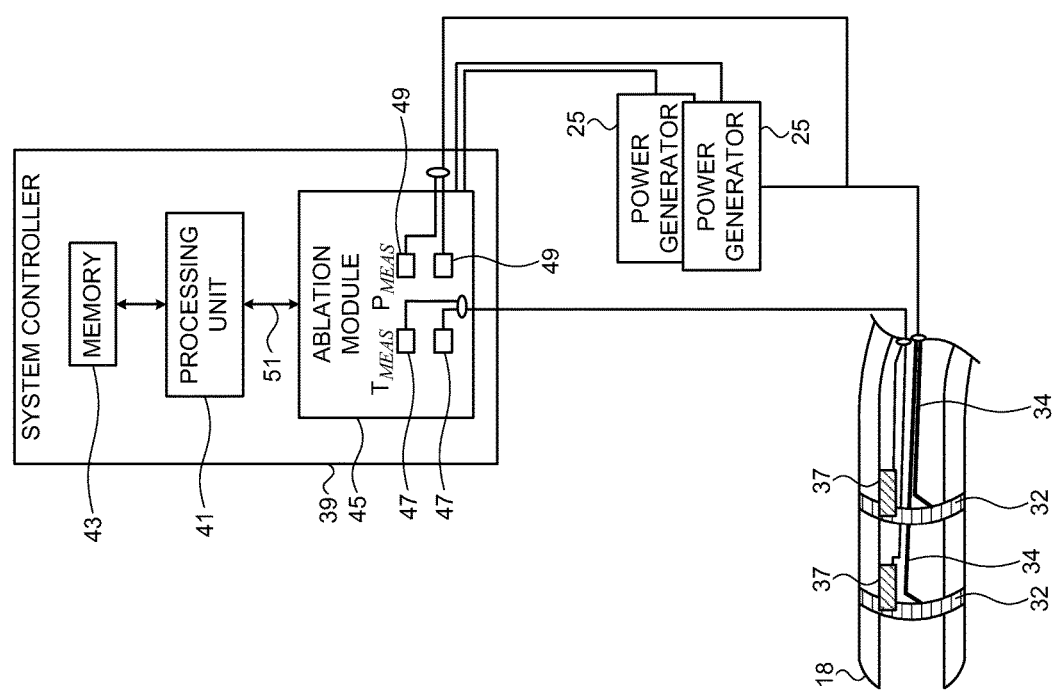
FIG. 2 is a schematic illustration of a controller for an ablation power generator, which is constructed and operative in accordance with a disclosed embodiment of the invention.

Reference is now made to FIG. 2, which is a schematic illustration of a controller 39 for the ablation power generator 25 (FIG. 1), which is constructed and operative in accordance with a disclosed embodiment of the invention. The controller 39 comprises a processing unit 41, a memory 43 for storing data and instructions for the processing unit 41, and an ablation module 45. In some embodiments, instances of the controller 39 may control respective electrodes 32 in a multi-electrode catheter. In such embodiments the operating parameters and limitations for the power control algorithm employed in the instances of the controller 39 may be set globally or independently.

The ablation module 45 receives temperature signals $T_{meas}$ from each temperature sensor 37 via a respective port 47 and measures instantaneous power level signals $P_{meas}$ from each ablation power generator 25 via a respective port 49. Only two instances of the electrodes 32, temperature sensor 37 and the ports 47, 49 are shown in FIG. 2 for simplicity.

The function of the controller 39 is to perform ablation while maintaining a given power output of the ablation power generator 25 as closely as possible.

The processing unit 41 determines a deviation between the measured power level $P_{meas}$ and a predetermined target power value; and a deviation between the measured temperature $T_{meas}$ and a predetermined target temperature. More specifically, the processing unit 41 compares the temperature signals and the power level signals with preset power target values $P_{targ}$ and temperature target values $T_{targ}$, and transmits a control signal on line 51 to the ablation module 45, which controls the ablation power generator 25 so as to produce a new current value $I_{new}$, which is the result of incrementing (or decrementing) an existing current value $I_{present}$:

The value of $I_{new}$ can be computed generally as follows:

$$I_{new} = I_{present} + k \text{ Function}\left\{\left(\frac{P_{targ} - P_{meas}}{P_{targ}}\right)\left(\frac{T_{targ} - T_{meas}}{T_{targ}}\right)\right\} \quad \text{Eq. (1)}$$

where k is a damping constant. The formula may take the following form:

$$I_{new} = I_{present} + kC\left(\frac{P_{targ} - P_{meas}}{P_{targ}}\right)\left(\frac{T_{targ} - T_{meas}}{T_{targ}}\right) \quad \text{Eq. (2)}$$

where C has the value −1 if both $P_{meas}$ and $T_{meas}$ are greater than $P_{targ}$ and $T_{targ}$, respectively, and +1 otherwise.

The function can be a minimum function.

$$I_{new} = I_{present} + k\text{Min}\left\{\left(\frac{P_{targ} - P_{meas}}{P_{targ}}\right)\left(\frac{T_{targ} - T_{meas}}{T_{targ}}\right)\right\}. \quad \text{Eq. (3)}$$

Power may be measured, for example, using the teachings of commonly assigned application Ser. No. 12/941,165, filed Nov. 8, 2010, which is herein incorporated by reference.

The controller 39 thus increments the current gradually until the ablator reaches the target power and temperature levels. If either the power or the temperature (or both) exceeds the target level, the controller 39 instructs the ablation power generator 25 to reduce the ablation current in order to avoid injury.

Typically inputs at ports 47, 49 are read 10 times per second. The following parameters are read: Voltage (V); Current (I); Temperature (T); ambient temperature (N). The values $P_{meas}$ and $T_{meas}$ and the impedance $Z_{meas}$ are computed from the general formulas:

$$P=V*I;$$

$$Z=V/I.$$

The impedance values are displayed for the operator and used to confirm continuity in the system.

In practice changes in current demand (dD) are subject to the following:
Maximum temperature for each electrode ($T_t$)
Maximum current per electrode
Maximum overall power ($P_t$)/(or Maximum current)
Patch connection. The impedance of the patch connection can be tracked using the methods disclosed in U.S. Patent Application Publication No. 2007/0060832, entitled "Detection of Skin Impedance", which is herein incorporated by reference. When operating in unipolar mode, a rise in impedance can indicate patch disconnection from the body surface.
Maximum temperature (32-60° C., typically 47° C.).
Minimum temperature (typically 27° C.).
Maximum impedance (measured for each electrode); typically 250Ω.
Minimum impedance (typically 50Ω).
Maximum electrode impedance change (typically 100Ω) occurring during a preset time interval (typically 3 sec) Exceeding this limitation incurs risk of tissue damage and subsequent thrombus formation.
Minimum flow rate (typically 6 ml/min).
Elapsed ablation time. This is situation dependent and is usually established by the operator prior to the procedure. A typical value is 60 seconds.

Initially, power demand is typically set at 250 units (corresponding to about 1 W) using a digital-to-analog converter, but can be increased up to 2048 units. In subsequent iterations, changes in power demand are can be calculated as follows:

$$\Delta D = D_0 * \text{Min}((P_t - P_{meas})/P_t, (T_t - T_{meas})/(T_t)) \quad \text{Eq. (4).}$$

where $D_0$ is a constant predefined change in the demand or power (250 units in the demand around 1 W of power). At each iteration, the current value (I) corresponding to the power $$D_i + 1 = D_i + \Delta D \quad \text{Eq. (5)}$$

is output onto the electrode.

However, if Min $((P_t - P_{meas})/P_t, (T_t - T_{meas})/(T_t)) > 1$, the equation $$\Delta D = D_0 \quad \text{Eq. (6)}$$

is used, in order to limit the increment in the power level. If $$\text{Min}((P_t - P_{meas})/P_t, (T_t - T_{meas})/(T_t)) < -1.1,$$

then the power output is set at 0 in order to allow the tissue to cool.

The iteration rate for the algorithm is typically 10/sec, but can be in the range of 5-50/sec.

If the current power is more than required, i.e., $P_t < P_{meas}$ or $T_t < T_{meas}$, then the value $\Delta D$ is negative and the power output will be decreased. Power is increased only when the current power is lower than desired and none of the above restrictions are exceeded.

In some cases ablation may continue when one or more of the above-noted limitations are violated, but in a restricted mode of operation. The following example is illustrative:

1. If the power required (Demand) exceeds available power (MaxDemand) or the electrode temperature exceeds its maximum, ablation may continue in restricted mode at suboptimum power.

In other cases, ablation is terminated, as illustrated by the following examples:

2. An abrupt change in impedance that exceeds a limiting value signifies a potentially hazardous condition, e.g., a surface skin patch may be become disconnected.
3. Exceeding the maximum temperature limit, which can be caused by failure of a cooling pump.
4. Failing to exceed the minimum temperature. This is a safeguard, intended to prevent inadvertent ablation of tissues other than the target tissue. Violation of this threshold causes the ablation to terminate
5. Power output exceeding $P_t$ may indicate a short circuit.
6. Elapsed ablation time has exceeded a maximum limit. Although ablation terminates in this event, this is done for operational reasons, and not because of hardware failure.
7. Violating the minimum flow rate. This may indicate pump failure. The flow rate is typically tested functionally at the beginning of a procedure, before energizing the ablation power generator 25 (FIG. 2). An electrode temperature reduction of 1-3° C. is expected when the pump is energized.

Alternate Embodiment 1

Figure 3:
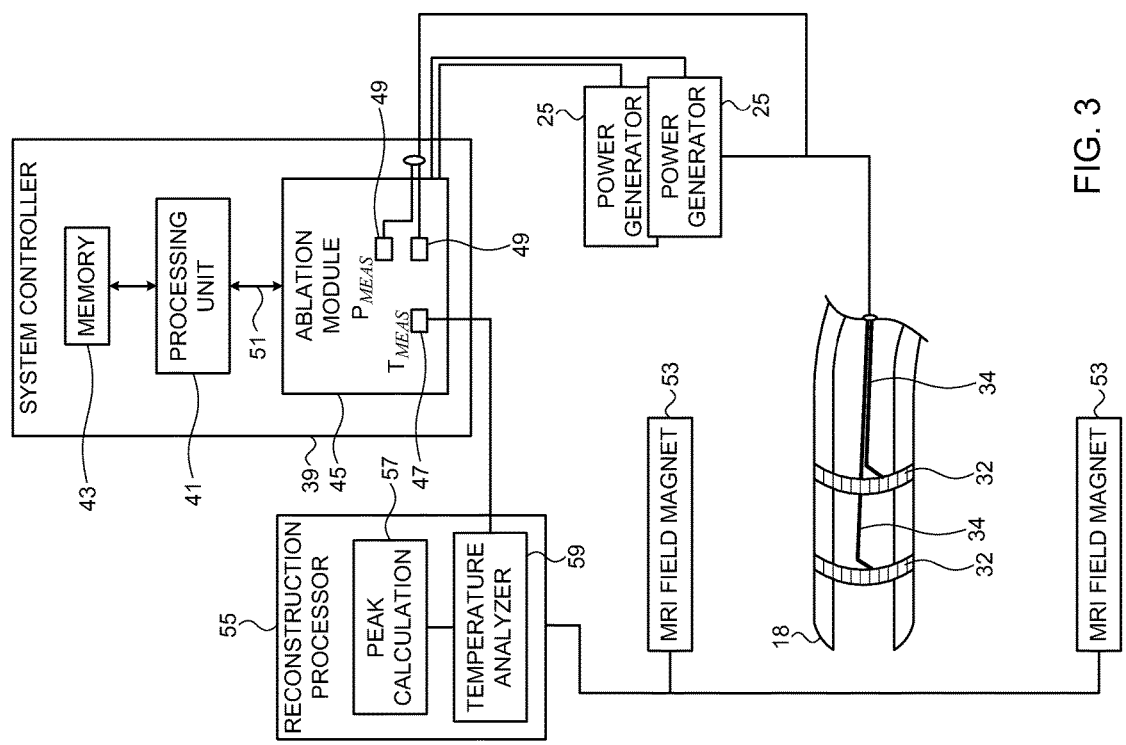
FIG. 3 is a schematic illustration of a controller for an ablation power controlled by a temperature sensor based on magnetic resonance imaging (MRI) analysis, which is constructed and operative in accordance with an alternate embodiment of the invention.

Reference is now made to FIG. 3, which is a schematic illustration of the controller 39 for the ablation power generator 25 (FIG. 1), which is constructed and operative in accordance with an alternate embodiment of the invention. In this embodiment the temperature sensors 37 (FIG. 2) may be omitted, which reduces manufacturing costs. Indication of the tissue temperature can be obtained by concurrently performing magnetic resonance imaging (MRI), directed at the target tissue. Dependencies of T1, T2, and proton density on temperature are used to relate change in signal strength to temperature.

MRI signals from field magnets 53 are acquired by a reconstruction processor 55, which is enhanced by a peak calculation module 57 that is linked to a temperature analyzer 59. The temperature analyzer 59 provides a thermometry signal to the port 47 of the ablation module 45. Thus, the MRI system operates as a temperature sensor for purpose of ablation control. The thermometry techniques presented in the following article can be used mutatis mutandis in this embodiment: TEMPANY, CLARE, M. D. JALIL AFNAN, and NATHAN MCDANNOLD, "Focused ultrasound ablation offer prostate cancer option." *Diagnostic Imaging* 31.1, Jan. 1, 2009.

Alternate Embodiment 2

Figure 4:
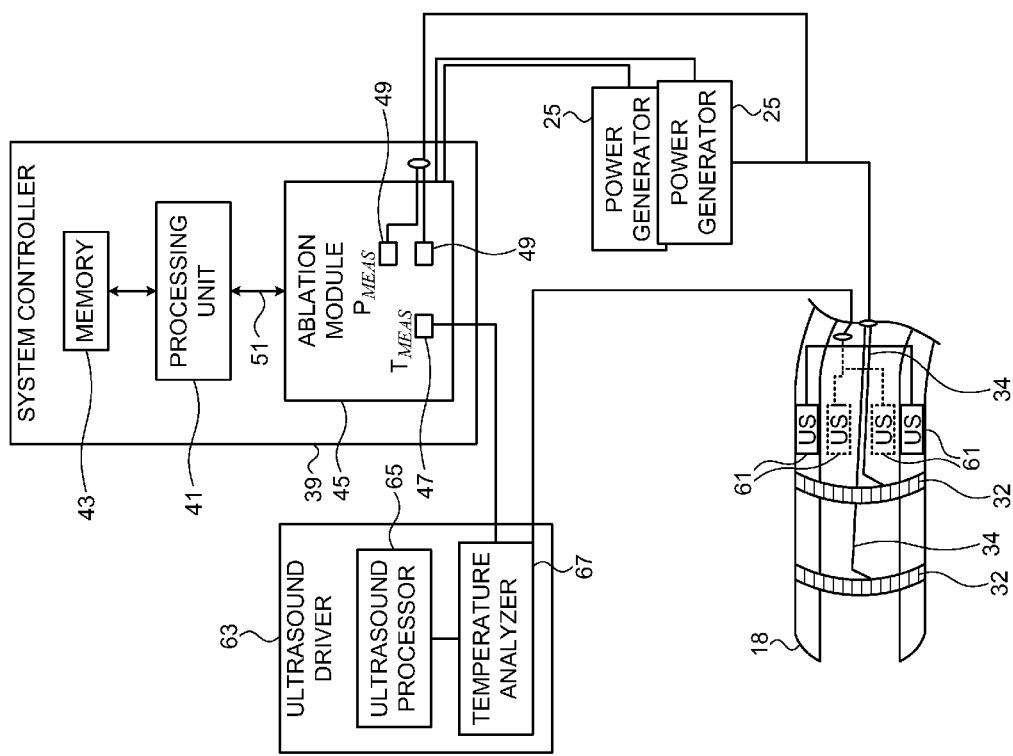
FIG. 4 is a schematic illustration of a controller for an ablation power controlled by a temperature sensor based on ultrasound analysis, which is constructed and operative in accordance with an alternate embodiment of the invention.

Reference is now made to FIG. 4, which is a schematic illustration of the controller 39 for the ablation power generator 25 (FIG. 1), which is constructed and operative in accordance with yet another alternate embodiment of the invention. In this embodiment the temperature sensors 37 (FIG. 2) may be omitted. Tissue temperature are measured by assessing thickness of the tissues being ablated, using the teachings described in commonly assigned U.S. application Ser. No. 11/357,512, entitled "Lesion Assessment by Pacing", which is hereby incorporated by reference.

An array of ultrasound transducers 61 is placed generally near the distal tip 18 of the catheter 14 (FIG. 1), and are energized by an ultrasound driver 63. One example of a suitable ultrasound driver that can be used for this purpose is an AN2300™ ultrasound system produced by Analogic Corporation, Centennial Drive, Peabody, Mass. Ultrasound driver 63 may support different imaging modes such as B-mode, M-mode, CW Doppler and color flow Doppler, as are known in the art.

Signals from the transducers 61 are received in an ultrasound processor 65, and further analyzed in a temperature analyzer 67. The temperature analyzer 67 provides a thermometry signal to the port 47 of the ablation module 45. A sub-system comprising the ultrasound components described in this embodiment functions as a temperature sensor for purposes of ablation control.

Alternate Embodiment 3

The energy sources in the previous embodiments produce RF energy. However, the invention can be carried out using other energy types. For example, in the embodiment of FIG. 4, the electrodes 32 (FIG. 2) can be omitted, and the transducers 61 configured to emit higher levels of ultrasound energy as taught in commonly assigned U.S. Pat. No. 7,156,816, which is herein incorporated by reference.

Alternatively, the source of ablative energy may be a laser, as disclosed in commonly assigned U.S. Pat. No. 6,997,924, which is herein incorporated by reference.

In either case temperature may be measured using any of the embodiments disclosed above.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method of body tissue ablation, comprising the steps of:
    inserting a probe into a body of a living subject;
    urging the probe into contact with a tissue in the body;
    generating ablative energy at a power output level at a level of current;
    transmitting the generated energy into the tissue via the probe;
    determining a measured temperature of the tissue and a measured power level of the generated energy during the step of transmitting the generated energy into tissue via the probe, via a temperature sensor and a power sensor;
    determining a power deviation by comparing a difference between the measured power level and a predetermined target power level;
    determining a temperature deviation by comparing a difference between the measured temperature of the tissue and a predetermined target temperature;
    calculating a target current value from a control function; and via a controller, controlling the power output level responsively to the calculated target current value by incrementally adjusting the level of current to the target current value gradually over time to generate energy at a new power output level until the measured temperature of the tissue and the measured power level each reach the predetermined target power level and the predetermined target temperature respectively, wherein the control function is:

$$I_{i+1} = I_i + k\text{Min}\left(\left(\frac{P_{targ} - P_{meas}}{P_{targ}}\right)\left(\frac{T_{targ} - T_{meas}}{T_{targ}}\right)\right),$$

or $$I_{i+1} = I_i + kC\left(\left(\frac{P_{targ} - P_{meas}}{P_{targ}}\right)\left(\frac{T_{targ} - T_{meas}}{T_{targ}}\right)\right),$$

wherein:
  $I_{i+1}$ is the target current value;
  $I_i$ is the target current value of a previous iteration;
  $P_{meas}$ is the measured power level;
  $P_{targ}$ is the target power level;
  $T_{meas}$ is the measured temperature;
  $T_{targ}$ is the target temperature;
  k is a damping constant; and
  C is a constant having a value of −1 if both $P_{meas}$ is greater than $P_{targ}$ and $T_{meas}$ is greater than $T_{targ}$, and +1 otherwise.

2. The method according to claim 1, wherein the generated energy is radiofrequency energy.

3. The method according to claim 1, wherein the generated energy is ultrasound energy.

4. The method according to claim 1, wherein the generated energy is laser-produced light energy.

5. The method according to claim 1, wherein determining a measured temperature is performed using magnetic resonance imaging analysis.

6. The method according to claim 1, wherein determining a measured temperature is performed using ultrasound imaging analysis.

7. The method according to claim 1, wherein the determining the power deviation, determining the temperature deviation, calculating the target current value, and controlling the power output level are iterated 10 times per second.

8. The method according to claim 1, wherein the determining the power deviation, determining the temperature deviation, calculating the target current value, and controlling the power output level are iterated 5-50 times per second.

9. The method according to claim 1, wherein the controlling the power output level is performed by limiting an increment or decrement thereof so as not to exceed a predetermined limiting condition, wherein the limiting condition is selected from the group consisting of a maximum current, a minimum electrode temperature, a maximum electrode temperature, a maximum temperature of the tissue, and a maximum power demand.

10. An ablation apparatus, comprising:
  a catheter having a distal portion for insertion into a body cavity of a living subject and configured to bring the distal portion into contact with a tissue in the body cavity;
  a power generator for generating ablative energy at a power output level having a level of current;
  an ablation electrode disposed on the distal portion configured to accept the energy from the power generator via the catheter and to conduct the energy to the tissue for ablation thereof;
  a temperature sensor disposed on the distal portion for determining a temperature of the ablation electrode; and
  a processor operative for determining a measured temperature of the tissue and a measured power level of the energy conducted through the ablation electrode, the processor configured to: determine a power deviation by comparing a difference between the measured power level and a predetermined target power level; determine a temperature deviation by comparing a difference between the measured temperature of the tissue and a predetermined target temperature; calculate a target current value from a control function; and control the power output level responsively to the calculated target current value by incrementally adjusting the level of current to the target current value gradually over time to generate energy at a new power output level until the measured temperature of the tissue and the measured power level each reach the predetermined target power level and the predetermined target temperature respectively, wherein the control function is:

$$I_{i+1} = I_i + k\text{Min}\left(\left(\frac{P_{targ} - P_{meas}}{P_{targ}}\right)\left(\frac{T_{targ} - T_{meas}}{T_{targ}}\right)\right),$$

or $$I_{i+1} = I_i + kC\left(\left(\frac{P_{targ} - P_{meas}}{P_{targ}}\right)\left(\frac{T_{targ} - T_{meas}}{T_{targ}}\right)\right),$$

wherein:
  $I_{i+1}$ is the target current value;
  $I_i$ is the target current value of a previous iteration;
  $P_{meas}$ is the measured power level;
  $P_{targ}$ is the target power level;
  $T_{meas}$ is the measured temperature;
  $T_{targ}$ is the target temperature;
  k is a damping constant; and
  C is a constant having a value of −1 if both $P_{meas}$ is greater than $P_{targ}$ and $T_{meas}$ is greater than $T_{targ}$, and +1 otherwise.

11. The ablation apparatus according to claim 10, wherein the generated energy is radiofrequency energy.

12. The ablation apparatus according to claim 10, wherein the processor is configured to determine the power deviation, determine the temperature deviation, calculate the target current value and control the power output level iteratively 10 times per second.

13. The ablation apparatus according to claim 10, wherein the processor is configured to determine the power deviation, determine the temperature deviation, calculate the target current value from the control function and control the power output level iteratively 5-50 times per second.

14. The ablation apparatus according to claim 10, wherein the processor is configured to control the power output level by limiting an increment or decrement thereof so as not to exceed a predetermined limiting condition, wherein the limiting condition is selected from the group consisting of a maximum current, a minimum electrode temperature, a maximum electrode temperature, a maximum temperature of the tissue, and a maximum power demand.

* * * * *